United States Patent
Kim et al.

(10) Patent No.: US 12,318,248 B2
(45) Date of Patent: Jun. 3, 2025

(54) ULTRASOUND DIAGNOSIS APPARATUS AND DIAGNOSIS METHOD

(71) Applicant: SAMSUNG MEDISON CO., LTD., Gangwon-do (KR)

(72) Inventors: Do Gyun Kim, Gangwon-do (KR); Min Joong Park, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 134 days.

(21) Appl. No.: 18/115,221

(22) Filed: Feb. 28, 2023

(65) Prior Publication Data

US 2024/0074726 A1    Mar. 7, 2024

(30) Foreign Application Priority Data

Sep. 2, 2022 (KR) .................. 10-2022-0111711

(51) Int. Cl.
*A61B 8/08* (2006.01)
*A61B 8/00* (2006.01)

(52) U.S. Cl.
CPC ............ *A61B 8/0866* (2013.01); *A61B 8/466* (2013.01); *A61B 8/5223* (2013.01)

(58) Field of Classification Search
CPC ..... A61B 8/0866; A61B 8/466; A61B 8/5223; A61B 8/4427; A61B 8/4461; A61B 8/4477; A61B 8/4494; A61B 8/464; A61B 8/5207; A61B 8/4405; A61B 8/085; A61B 8/4472; A61B 8/4488; A61B 8/461; A61B 8/565; A61B 8/0833; A61B 8/463; A61B 8/465; A61B 8/469; A61B 8/5215
See application file for complete search history.

(56) References Cited

U.S. PATENT DOCUMENTS

| | | | |
|---|---|---|---|
| 10,898,298 B1 * | 1/2021 | Raslambekov | ........ A61B 6/032 |
| 10,905,400 B2 | 2/2021 | Day | |
| 2018/0185003 A1 | 7/2018 | Zou et al. | |
| 2020/0170614 A1 | 6/2020 | Kim et al. | |
| 2021/0015449 A1 | 1/2021 | Brandl et al. | |

(Continued)

FOREIGN PATENT DOCUMENTS

| | | | |
|---|---|---|---|
| CN | 111738879 | * | 10/2020 |
| EP | 3858249 A1 | | 8/2021 |
| EP | 3964136 A1 | | 3/2022 |

(Continued)

OTHER PUBLICATIONS

Feng et al., Automatic Fetal Face Detection From Ultrasound Volumes Via Learning 3D and 2D Information. 2009 IEEE. pp. 2488-2495 (Year: 2009).*

(Continued)

*Primary Examiner* — Alexei Bykhovski
(74) *Attorney, Agent, or Firm* — Morgan Lewis & Bockius LLP

(57) ABSTRACT

An ultrasound diagnosis apparatus according to an embodiment of the present disclosure includes an acquirer configured to acquire an ultrasound image, an analyzer configured to analyze appearances of a fetus using the image acquired in the acquirer, and a sorter configured to sort out the image of the fetus corresponding to a target of interest among the appearances of the fetus analyzed in the analyzer.

15 Claims, 13 Drawing Sheets

(56) References Cited

U.S. PATENT DOCUMENTS

2023/0100874 A1\* 3/2023 Wu .................. G06V 40/28
726/19

FOREIGN PATENT DOCUMENTS

| | | |
|---|---|---|
| JP | 2021-122705 A | 8/2021 |
| KR | 10-2002-0045196 A | 6/2002 |
| KR | 10-2006-0106535 A | 10/2006 |
| KR | 10-1114621 B1 | 2/2012 |
| KR | 10-2016-0064889 A | 6/2016 |
| KR | 10-1978728 B1 | 5/2019 |
| KR | 10-2108422 B1 | 4/2020 |
| KR | 10-2021-0072202 A | 6/2021 |

OTHER PUBLICATIONS

Lebit, et al. (The Role of 4D Ultrasound in the Assessment of Fetal Behaviour, Medica—A Journal of Clinical Medicine, vol. 6, No. 2, 2011) (Year: 2011).\*
Extended European Search Report dated Aug. 11, 2023 issued in European Patent Application No. 23158093.7.
F-D Lebit, et al., "The Role of 4D Ultrasound in the Assessment of Fetal Behaviour," Medica—A Journal of Clinical Medicine, vol. 6, No. 2, 2011.

\* cited by examiner (c)　　　　　　　　(d)

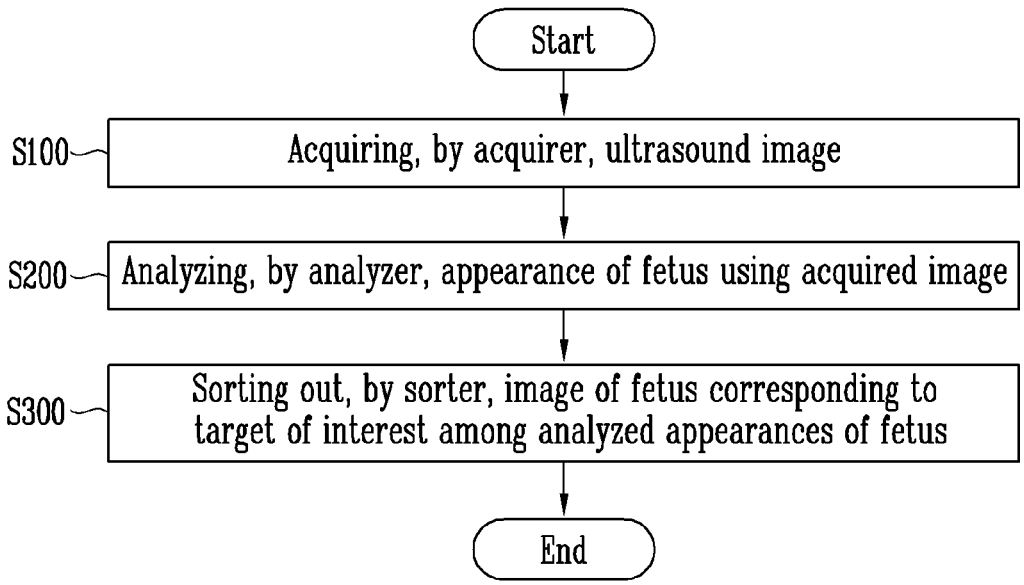

FIG. 12
Second quarter
Yawning 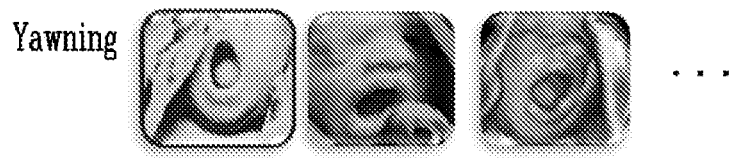 ...
Sticking tongue out 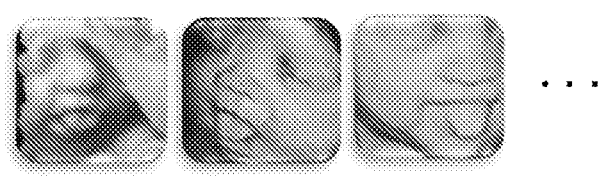 ...
Third quarter
Yawning 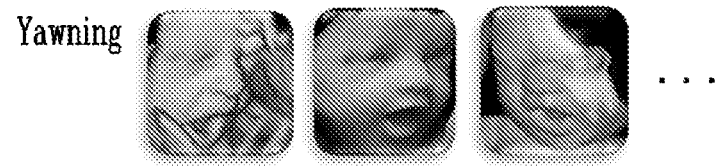 ...

ULTRASOUND DIAGNOSIS APPARATUS AND DIAGNOSIS METHOD

CROSS-REFERENCE TO RELATED APPLICATION

The present application claims priority under 35 U.S.C. § 119(a) to Korean patent application number 10-2022-0111711 filed on Sep. 2, 2022, in the Korean Intellectual Property Office, the entire disclosure of which is incorporated by reference herein.

BACKGROUND

1. Technical Field

The present disclosure relates to an ultrasound diagnosis apparatus and a diagnosis method, and more particularly, to an ultrasound diagnosis apparatus and a diagnosis method, capable of automatically sorting out an image in which a specific motion of a fetus is shown from among images of the fetus captured by ultrasound.

2. Related Art

Ultrasound imaging refers to imaging of sound waves reflected from the inside of a human body after sending high-frequency sound waves from a surface of the human body to the inside and the ultrasound examination provides ultrasound images in real time. Conventionally, an ultrasound diagnosis apparatus is being changed from an analog type to a digital type as well as from 2D ultrasound diagnosis apparatuses to 3D and then 4D ultrasound diagnosis apparatuses that include the passage of time. Recently, 4D ultrasound diagnosis examination is also being applied, which shows the movement of 3D images.

The ultrasound diagnosis apparatus is an apparatus which irradiates ultrasound signals generated from a transducer of a probe to an object and receives information of echo signals reflected from the object to acquire an image of an internal part of the object. Such the ultrasound diagnosis apparatus exhibits higher stability than a diagnosis apparatus using X-rays while the real-time image display is possible, thereby being widely used along with other imaging diagnosis apparatuses.

In particular, compared to other counterparts, ultrasound diagnosis apparatuses that secure high accuracy as well as safety with no risk of radiation exposure to the human body are being widely used in the process of diagnosing pregnant women and fetuses. In addition, most hospitals use the ultrasound diagnosis apparatus to check the growth of the fetus and, for mothers, to predict an appearance of the fetus through ultrasound images.

SUMMARY

Embodiments provide an ultrasound diagnosis apparatus and a diagnosis method, capable of easily providing an image that a mother desires by automatically sorting and displaying an image including a specific motion of a fetus when photographing fetal ultrasound images.

In accordance with an aspect of the present disclosure, there is provided an ultrasound diagnosis apparatus, including an acquirer configured to acquire an ultrasound image, an analyzer configured to analyze appearances of a fetus using the image acquired in the acquirer, and a sorter configured to sort out the image of the fetus corresponding to a target of interest among the appearances of the fetus analyzed in the analyzer.

Specifically, the ultrasound diagnosis apparatus may include a target-of-interest storage configured to store the image sorted out by the sorter.

Specifically, the target of interest may be at least one of yawning, hand sucking, foot sucking, and tongue sticking out motions of the fetus.

Specifically, the acquirer may be configured to detect a sagittal plane in which the position of the mouth is shown in the image.

Specifically, the analyzer may be configured to analyze at least one of a shape of a mouth, a position of a tongue, and a position of a hand or foot of the fetus.

Specifically, the analyzer may be configured to measure, through a 3D image, a vertical length from the center of an upper lip to the center of a lower lip of the fetus as well as a horizontal length measured by setting left and right sides of the fetal lips as both endpoints so as to analyze that the fetus is opening its mouth when the vertical length is more than a predetermined multiple of the horizontal length.

Specifically, the analyzer may be configured to analyze, through a sagittal plane in which a position of the mouth in the image is shown, that the fetus is opening its mouth when an oval corresponding to a circumference of a skull of the fetus is cut off at a position of the fetal mouth.

Specifically, through a sagittal plane analyzed by the analyzer as opening the mouth, when it is determined that a gap between the lips of the fetus increases for a predetermined amount of time, the sorter classifies the image as the yawning motion of the fetus.

Specifically, the analyzer may be configured to determine whether at least one of a hand and a foot of the fetus is positioned around a mouth of the fetus from at least one of a 3D image and a 2D image.

Specifically, after identifying a sagittal plane in which positions of the mouth and hand or the mouth and foot of the fetus are all shown in the left and right directions of the fetal mouth, the analyzer may be configured to measure, through the sagittal plane, a distance between the mount and hand or the mouth and foot of the fetus so as to analyze that the hand or foot is put in the mouth when the measured distance is less than or equal to a predetermined value.

Specifically, through the 3D image of the image analyzed by the analyzer that the hand or foot is put in the mouth, when it is determined that there is a movement of the fetal mouth, the sorter may be configured to classify the image as a hand sucking or foot sucking motion of the fetus.

Specifically, after identifying the 3D image in which the mouth and a tongue of the fetus are all shown in left and right directions of the fetal mouth, the analyzer may be configured to analyze, through the 3D image, that the fetus is sticking out the tongue when a part of an upper or lower lip of the fetus is invisible by being hidden by the tongue.

Specifically, through a sagittal plane, when it is determined that a position of a tongue of the fetus is beyond a base line of the fetal mouth, the sorter may be configured to classify the image as a tongue sticking out motion of the fetus.

Specifically, the ultrasound diagnosis apparatus may further include an extractor configured to extract a high-quality image from images sorted out when the images overlap.

Specifically, the ultrasound diagnosis apparatus may include a display unit configured to display the image sorted out on a screen.

Specifically, the display unit may be configured to simultaneously display a plurality of the images sorted out.

Specifically, the display unit may be configured to display a notification when the appearance of the fetus corresponds to the target of interest.

Specifically, the display unit may further include a selector configured to select an image to be displayed on the screen from among images sorted out.

Specifically, the display unit may be configured to display a period of pregnancy of a mother corresponding to the image of the fetus.

Specifically, the image displayed on the display unit may be at least one of a 2D image, a 3D image, and a 4D image with passage of time.

In accordance with another aspect of the present disclosure, there is provided an ultrasound diagnosis method, including acquiring, by an acquirer, an ultrasound image, analyzing, by an analyzer, appearances of a fetus using the acquired image, and sorting out, by a sorter, the image of the fetus corresponding to a target of interest among the analyzed appearances of the fetus.

Specifically, the method may include storing, by a target-of-interest storage, the image sorted out.

Specifically, the sorting out of the image may include determining whether the appearance of the fetus analyzed by the analyzer corresponds to the target of interest, and classifying the image of the fetus determined as the target of interest.

Specifically, the method may further include determining a yawning motion of the fetus, and the determining of the yawning motion of the fetus may include measuring, by the analyzer, through a 3D image, a vertical length from the center of an upper lip to the center of a lower lip of the fetus as well as a horizontal length measured by setting left and right sides of the fetal lips as both endpoints so as to analyze that the fetus is opening its mouth when the vertical length is more than a predetermined multiple of the horizontal length, and through a sagittal plane of the image analyzed by the analyzer as opening the mouth, when it is determined that a gap between the lips of the fetus increases for a predetermined amount of time, classifying the image, by the sorter, as the yawning motion of the fetus.

Specifically, the method may include analyzing, by the analyzer, through the sagittal plane including the mouth in the image, that the fetus is opening the mouth, when an oval corresponding to a circumference of a skull of the fetal is cut off at a position corresponding to the fetal mouth.

Specifically, the method may further include determining a hand sucking or foot sucking motion of the fetus, and the determining of the hand sucking or foot sucking motion of the fetus may include checking, by the analyzer, a sagittal plane in which positions of a hand or foot and a mouth of the fetus are all shown in left and right directions of the fetal mouth, measuring, by the analyzer, through the sagittal plane, a distance between the mouth and hand or the mouth and foot of the fetus to analyze that the hand or foot is put in the mouth when the analyzed distance is less than or equal to a predetermined value, and through a 3D image of the image analyzed by the analyzer that the hand or foot is put in the mouth, when it is determined that there is a movement of the fetal mouth, classifying the image, by the sorter, as the hand sucking or foot sucking motion of the fetus.

Specifically, the method may further include determining a tongue sticking out motion of the fetus, and the determining of the tongue sticking out motion of the fetus may include identifying, by the analyzer, a 3D image in which both a mouth and a tongue of the fetus are shown in left and right directions of the mouth of the fetus, analyzing, by the analyzer, through the 3D image, that the fetus is sticking out the tongue when a part of an upper or a lower lip of the fetus is invisible by being hidden by the tongue, and through a sagittal plane including the mouth in the image analyzed by the analyzer as the fetus sticking out the tongue, classifying the image, by the sorter, as the tongue sticking out motion of the fetus when it is determined that a position of the fetal tongue is beyond a base line of the fetal mouth.

Specifically, the method may include displaying, by a display unit, the image sorted out on a screen.

An ultrasound diagnosis apparatus and a diagnosis method according to example embodiments of the present disclosure may easily provide an image that a mother is interested in, by determining with high accuracy whether the appearance of a fetus in an ultrasound diagnosis image corresponds to a target of interest.

The effect of the present disclosure is not limited to the above-mentioned effects, and the effects not mentioned may be clearly understood by those of ordinary skill in the art to which the present disclosure pertains from the present specification and the accompanying drawings.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

FIG. 10 is a flowchart illustrating an ultrasound diagnosis method in accordance with an embodiment of the present disclosure.

FIG. 11 is a diagram for explaining content displayed on a display unit of the ultrasound diagnosis apparatus 700 in accordance with an embodiment of the present disclosure.

FIG. 12 is a diagram for explaining content displayed on the display unit of the ultrasound diagnosis apparatus 700 in accordance with another embodiment of the present disclosure.

DETAILED DESCRIPTION

Figure 1:
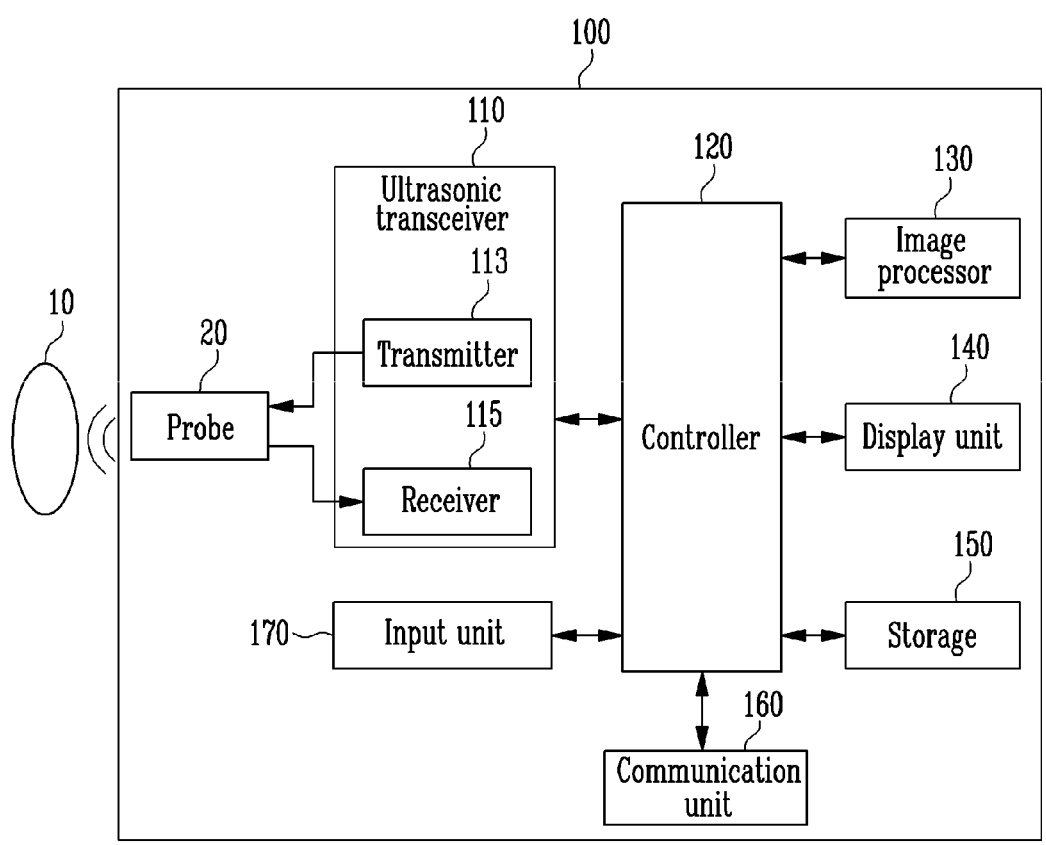
FIG. 1 is a block diagram illustrating a configuration of an ultrasound diagnosis apparatus 100 in accordance with any one embodiment of the present disclosure.

The present specification clarifies the scope of the present disclosure and, to enable those of ordinary skill in the art to which the present disclosure pertains to practice the present disclosure, the principle of the present disclosure is explained and embodiments are disclosed. The disclosed embodiments may be implemented in various forms.

Throughout the specification, when a part is "connected" to another part, it includes not only a case of being directly connected but also a case of being indirectly connected, and the indirect connection includes connection through a wireless communication network.

In addition, terms used herein are used to describe the embodiments, not intended to limit and/or restrict the disclosed invention. The singular expression includes the plural expression unless the context clearly dictates otherwise. In the present specification, terms such as "comprise" or "have" specify the presence of stated features, integers, steps, operations, elements, components or a combination thereof, but do not preclude the presence or addition of one or more other features, integers, steps, operations, elements, components, and/or groups thereof.

Further, although terms including ordinal numbers such as "first," "second," and the like are used to explain various components, the components are not limited to such terms. These terms are used only to distinguish one component from another component. For example, a first component may be referred to as a second component, or similarly, the second component may be referred to as the first component within the scope of the present disclosure.

In addition, terms such as "unit", "group", "block", "member", and "module" may refer to a unit that processes at least one function or operation. For example, the terms may refer to at least one process processed by at least one hardware such as a field-programmable gate array (FPGA)/application specific integrated circuit (ASIC), at least one software stored in a memory, or a processor.

Symbols given to each step are used to identify each step, and these signs do not indicate the order between the steps. Each step may be performed differently from the stated order unless the context clearly indicates a specific order.

In addition, an image herein may include a medical image acquired by a medical imaging apparatus such as a magnetic resonance imaging (MRI) apparatus, a computed tomography (CT) apparatus, an ultrasound imaging apparatus, or an X-ray imaging apparatus.

Also, the term 'object' as used herein refers to a subject to be photographed, and may include human, animal, or a part thereof. For example, the object may include a part of the body (such as organs) or a phantom.

Throughout the specification, the term "ultrasound image" as used herein refers to an image for an object transmitted to the object and processed based on an ultrasound signal reflected from the object.

Hereinafter, an embodiment according to the present disclosure will be described in detail with reference to the accompanying drawings.

FIG. 1 illustrates a block diagram showing a configuration of an ultrasound diagnosis apparatus 100 in accordance with any one embodiment of the present disclosure.

The ultrasound diagnosis apparatus 100 according to an embodiment of the present disclosure may include a probe 20, an ultrasonic transceiver 110, a controller 120, an image processor 130, a display unit 140, a storage 150, a communication unit 160, and an input unit 170.

The ultrasound diagnosis apparatus 100 may be provided not only as a cart type but also as a portable type. Examples of the portable ultrasound diagnosis apparatus may include a smart phone, a laptop computer, a PDA, and a tablet PC including a probe and an application, but are not limited thereto.

The probe 20 may include a plurality of transducers. The plurality of transducers may transmit an ultrasound signal to an object 10 according to a transmission signal applied from a transmitter 113. The plurality of transducers may be configured to receive the ultrasound signal reflected from the object 10 to generate a received signal. Also, the probe 20 may be integrated with the ultrasound diagnosis apparatus 100 or may be provided as a separate type connected to the ultrasound diagnosis apparatus 100 by a wire or wirelessly. Moreover, the ultrasound diagnosis apparatus 100 may include one or a plurality of probes 20 according to an implementation form.

The controller 120 is configured to control, in consideration of the position and focal point of the plurality of transducers included in the probe 20, the transmitter 113 to generate a transmission signal to be applied to each of the plurality of transducers.

The controller 120 is configured to convert the received signal received from the probe 20 from analog to digital and, in consideration of the positions and focal points of the plurality of transducers, add the digitally converted received signals to control the receiver 115 to generate ultrasound data.

The image processor 130 is configured to generate an ultrasound image by using the ultrasound data generated by the ultrasound receiver 115.

The display unit 140 may be configured to display the generated ultrasound image and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components of the ultrasound diagnosis apparatus 100. The controller 120 may include a memory configured to store a program or data for performing a function of the ultrasound diagnosis apparatus 100, and a processor configured to process a program or data. Also, the controller 120 may be configured to receive a control signal from the input unit 170 or an external device to control the operation of the ultrasound diagnosis apparatus 100.

The ultrasound diagnosis apparatus 100 may include the communication unit 160 and be connected with an external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules, and wireless communication modules.

It is also possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may execute a program stored in the server, so as to control the client device that is communicatively connected to the server to perform the method according to the disclosed embodiments.

The storage 150 may be configured to store various data or programs for driving and controlling the ultrasound diagnosis apparatus 100, input/output ultrasound data, and an acquired ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 2:
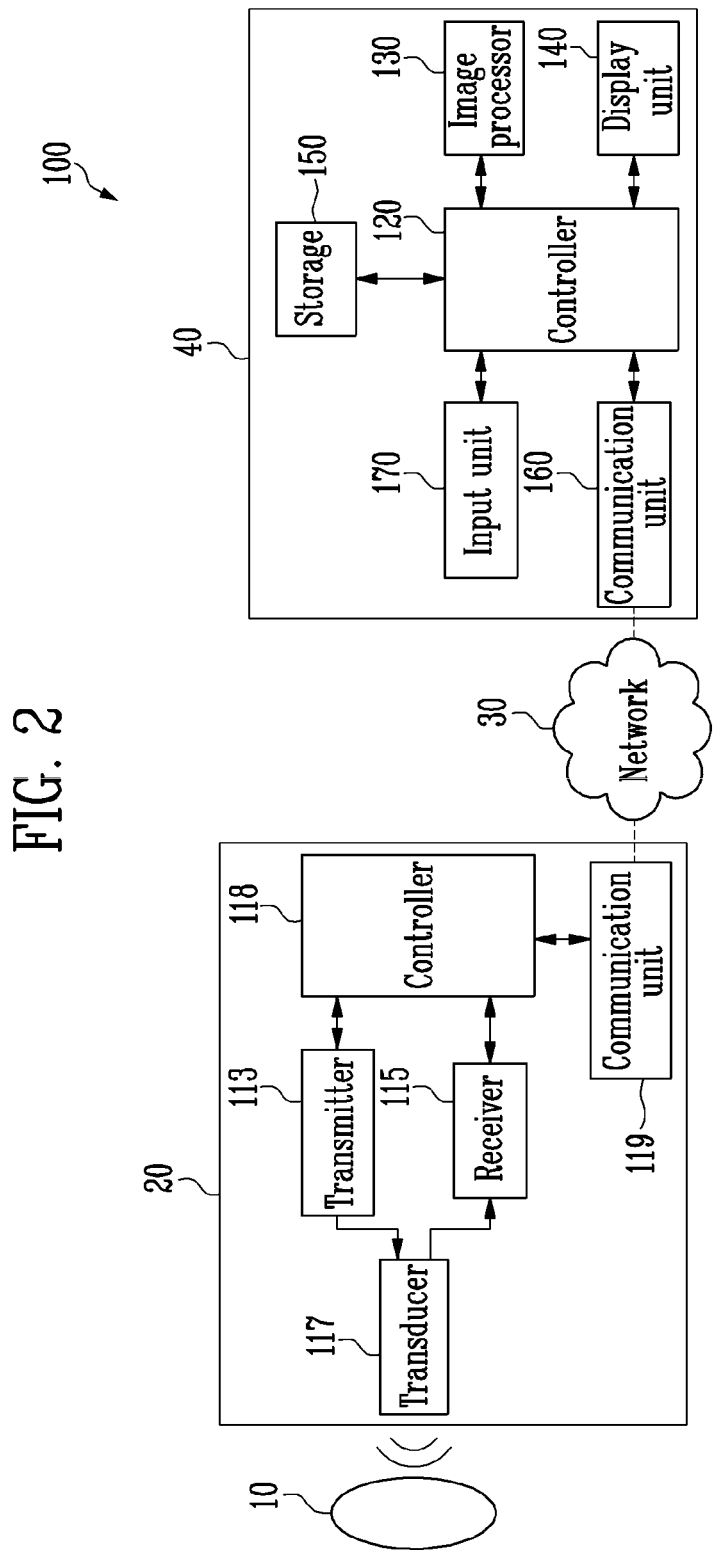
FIG. 2 is a block diagram illustrating a configuration of the ultrasound diagnosis apparatus 100 in accordance with any one embodiment of the present disclosure.

FIG. 2 illustrates a block diagram showing a configuration of the ultrasound diagnosis apparatus 100 in accordance with any one embodiment of the present disclosure.

Referring to FIG. 2, the ultrasound diagnosis apparatus 100 may include a wireless probe 20 and an ultrasound system 40.

The wireless probe 20 may include the transmitter 113, a transducer 117, a receiver 115, a controller 118, and a communication unit 119. It is shown in FIG. 2 that the wireless probe 20 includes both the transmitter 113 and the receiver 115, but depending on the implementation, the wireless probe 20 may include only a part of the configuration of the transmitter 113 and the receiver 115, and a part of the configuration of the transmitter 113 and the receiver 115 may be included in the ultrasound system 40. Alternatively, the wireless probe 20 may further include the image processor 130.

The transducer 117 may include a plurality of transducers. The plurality of transducers may be configured to transmit an ultrasound signal to the object 10 according to a transmission signal transmitted from the transmitter 113. The plurality of transducers may be configured to receive the ultrasound signal reflected from the object 10 to generate a received signal.

The controller 118 is configured to control the transmitter 113 to generate a transmission signal to be transmitted to each of the plurality of transducers in consideration of the positions and focal points of the plurality of transducers.

The controller 118 is configured to convert the received signal received from the transducer 117 from analog to digital and, in consideration of the positions and focal points of the plurality of transducers, sum up the digitally converted received signals to control the receiver 155 to generate ultrasound data. Alternatively, when the wireless probe 20 includes the image processor 130, it is possible to generate an ultrasound image using the generated ultrasound data.

The communication unit 119 may be configured to wirelessly transmit the generated ultrasound data or ultrasound image to the ultrasound system 40 through a wireless network. Alternatively, the communication unit 119 may be configured to receive a control signal and data from the ultrasound system 40.

Also, the ultrasound diagnosis apparatus 100 may include one or more wireless probes 20 according to an implementation form.

The ultrasound system 40 may be configured to receive ultrasound data or an ultrasound image from the wireless probe 20. The ultrasound system 40 may include the controller 120, the image processor 130, the display unit 140, the storage 150, the communication unit 160, and the input unit 170.

The image processor 130 may be configured to generate an ultrasound image by using the ultrasound data received from the wireless probe 20.

The display unit 140 may be configured to display an ultrasound image received from the wireless probe 20, an ultrasound image generated in the ultrasound system 40, and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components of the ultrasound diagnosis apparatus 100. The controller 120 may include a memory configure to store a program or data for performing a function of the ultrasound diagnosis apparatus 100, and a processor configure to process a program or data. Also, the controller 120 may be configured to receive a control signal from the input unit 170 or an external device to control the operation of the ultrasound diagnosis apparatus 100.

The ultrasound system 40 may include the communication unit 160 and be connected with the external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules and wireless communication modules.

It is also possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform the methods according to the disclosed embodiments. Alternatively, two or more of the server, the client device, and the third device may execute the program for perform the methods according to the disclosed embodiments by distributing the methods.

For example, a server (e.g., a cloud server or an artificial intelligence server, etc.) may be configured to execute a program stored in the server, so as to control the client device that is communicatively connected to the server to perform the methods according to the disclosed embodiments.

The storage 150 may be configured to store various data or programs for driving and controlling the ultrasound diagnosis apparatus 100, input/output ultrasound data, and an ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 3:
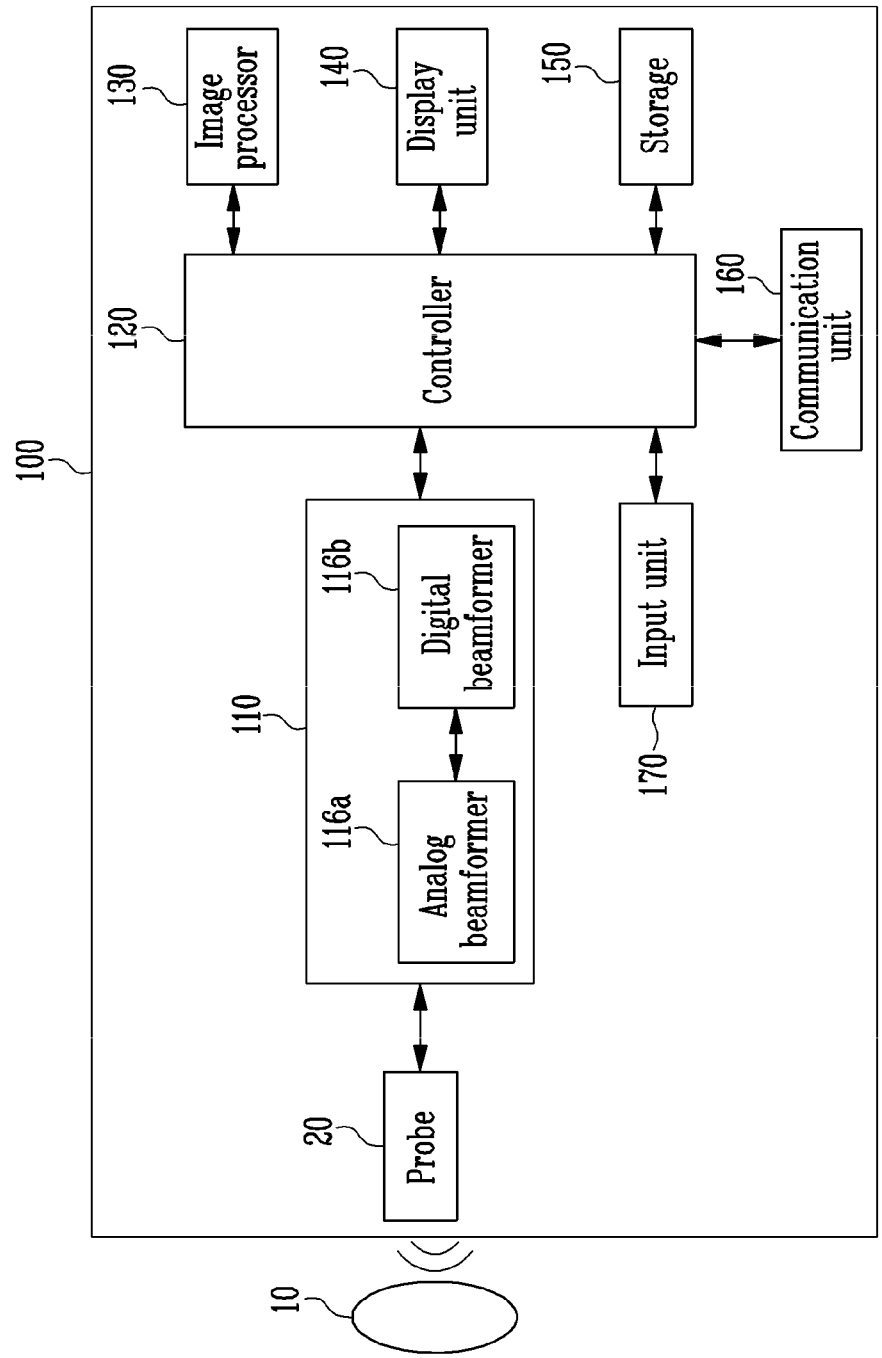
FIG. 3 is a block diagram illustrating a configuration of the ultrasound diagnosis apparatus 100 in accordance with any one embodiment of the present disclosure.

FIG. 3 illustrates a block diagram showing a configuration of the ultrasound diagnosis apparatus 100 in accordance with any one embodiment of the present disclosure.

Referring to FIG. 3, the ultrasound diagnosis apparatus 100 may include the probe 20, the ultrasonic transceiver 110, the controller 120, the image processor 130, the display unit 140, an input unit 170, the storage 150, and the communication unit 160.

The probe 20 according to an embodiment of the present disclosure may include a plurality of transducers. The plurality of transducers may be arranged in two dimensions to form a 2D transducer array.

For example, the 2D transducer array may have a form including a plurality of sub-arrays including a plurality of transducers arranged in a first direction and in a second direction different from the first direction.

Also, the ultrasonic transceiver 110 may include an analog beamformer 116a and a digital beamformer 116b. Though the ultrasonic transceiver 110 and the probe 20 are illustrated as having a separate configuration in FIG. 3, the probe 20 according to an embodiment of the present disclosure may include partial or entire configuration of ultrasonic transceiver 110 according to the implementation form. For example, the probe 20 may include one or both of the analog beamformer 116a and the digital beamformer 116b.

The controller 120 may be configured to calculate a time delay value for digital beamforming for each sub-array with respect to each of the plurality of sub-arrays included in the 2D transducer array. Also, the controller 120 may be configured to calculate a time delay value for analog beamforming with respect to each of the transducers included in any one of the plurality of sub-arrays.

The controller 120 may be configured to control, according to the time delay value for analog beamforming and the time delay values for digital beamforming, the analog beamformer 116a and the digital beamformer 116b to generate a transmission signal to be transmitted to each of the plurality of transducers.

Also, the controller 120 may be configured to control the analog beamformer 116a to sum up the signals received from the plurality of transducers for each sub-array according to the time delay value for analog beamforming. In addition, the controller 120 may be configured to control the ultrasonic transceiver 110 to convert the signal summed for each sub-array from analog to digital. In addition, the controller 120 may be configured to control the digital beamformer 116b to generate ultrasound data by summing the digitally converted signals according to the time delay value for digital beamforming.

The image processor 130 is configured to generate an ultrasound image using the generated ultrasound data.

The display unit 140 may be configured to display the generated ultrasound image and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components in the ultrasound diagnosis apparatus 100. The controller 120 may include a memory configured to store a program or data for performing a function of the ultrasound diagnosis apparatus 100 and a processor configured to process a program or data. Also, the controller 120 may be configured to receive a control signal from the input unit 170 or the external device to control the operation of the ultrasound diagnosis apparatus 100.

The ultrasound diagnosis apparatus 100 may include the communication unit 160 and be connected with the external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules and wireless communication modules.

It is possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits the control signal to the external device through the communication unit 160 to control the external device according to the control signal of the controller.

For example, the external device may be configured to process data of the external device according to the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform the methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may be configured to execute a program stored in the server, so as to control the client device that is communicatively connected to the server to perform the methods according to the disclosed embodiments.

The storage 150 may be configured to store various data or programs for driving and controlling the ultrasound diagnosis apparatus 100, input/output ultrasound data, and an ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 4A:
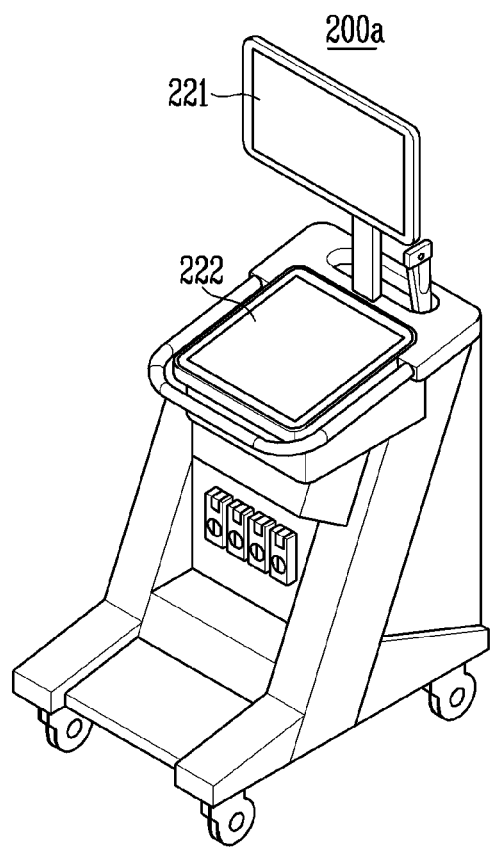
FIGS. 4A to 4C are perspective views of an ultrasound diagnosis apparatus 200 in accordance with at least one embodiment of the present disclosure.
Figure 4B:
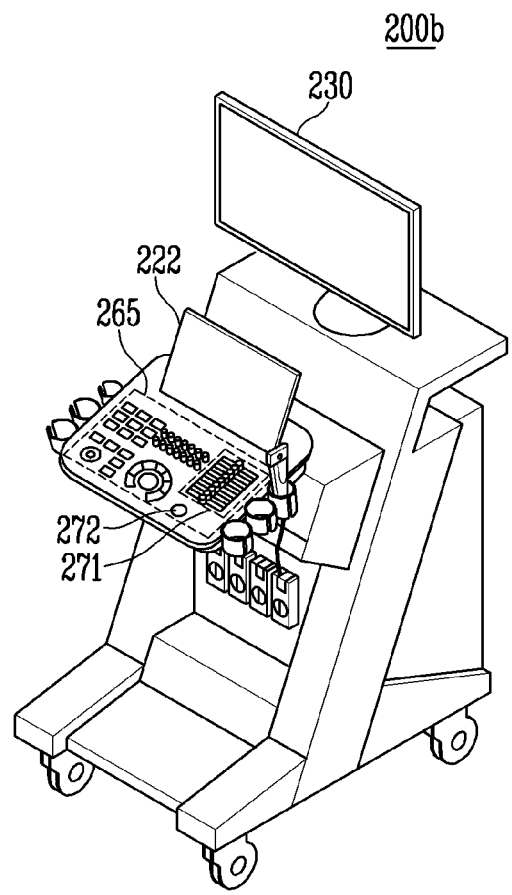
Figure 4C:
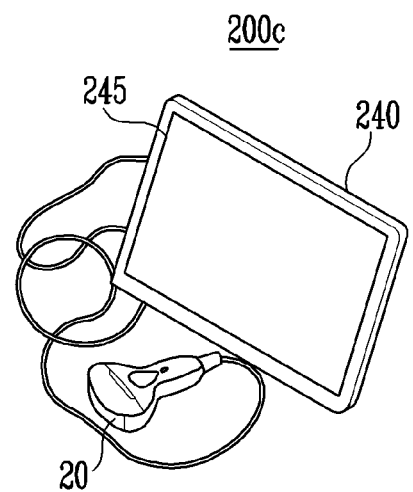

FIGS. 4A to 4C illustrate perspective views of an ultrasound diagnosis apparatus 200 in accordance with at least one embodiment of the present disclosure.

Referring to FIGS. 4A and 4B, the ultrasound diagnosis apparatuses 200a and 200b may include a main display unit 221 and a sub-display unit 222. One of the main display unit 221 and the sub-display unit 222 may be provided as a touch screen. The main display unit 221 and the sub-display unit 222 may be configured to display an ultrasound image or various information processed in the ultrasound diagnosis apparatuses 200a and 200b. In addition, the main display unit 221 and the sub-display unit 222 may be provided as a touch screen, and by providing a GUI, data for controlling the ultrasound diagnosis apparatuses 200a and 200b may be received from a user. For example, the main display unit 221 may be configured to display an ultrasound image, and the sub-display unit 222 may be configured to display a control panel for controlling the display of the ultrasound image in the form of a GUI. The sub-display unit 222 may be input with data for controlling the display of an image through a control panel displayed in the form of a GUI. The ultrasound diagnosis apparatuses 200a and 200b may be configured to control the display of the ultrasound image displayed on the main display unit 221 by using the received control data.

Referring to FIG. 4B, the ultrasound diagnosis apparatus 200b may further include a control panel 265 in addition to the main display unit 221 and the sub-display unit 222. The control panel 265 may include a button, a trackball, a jog switch, and a knob, and may be input with data for controlling the ultrasound diagnosis apparatus 200b from a user. For example, the control panel 265 may include a time gain compensation (TGC) button 271, and a freeze button 272. The TGC button 271 is a button for setting a TGC value for each depth of the ultrasound image. Also, when an input of the freeze button 272 is sensed while scanning the ultrasound image, the ultrasound diagnosis apparatus 200b may maintain a state in which a frame image at a corresponding moment is displayed.

In addition, the button, the track ball, the jog switch and the knob included in the control panel 265 may be provided to the main display unit 221 or the sub-display unit 222 as a GUI.

Referring to FIG. 4C, the ultrasound diagnosis apparatus 200c may be implemented as a portable type. Examples of the portable ultrasound diagnosis apparatus 200c may include smart phones, laptop computers, PDAs, and tablet PCs including a probe and an application, but are not limited thereto.

The ultrasound diagnosis apparatus 200c may include the probe 20 and a main body 240, and the probe 20 may be connected to one side of the main body 240 by a wire or wirelessly. The main body 240 may include a touch screen 245. The touch screen 245 may be configured to display an ultrasound image, various information processed in the ultrasound diagnosis apparatus, and a GUI.

Figure 5A:
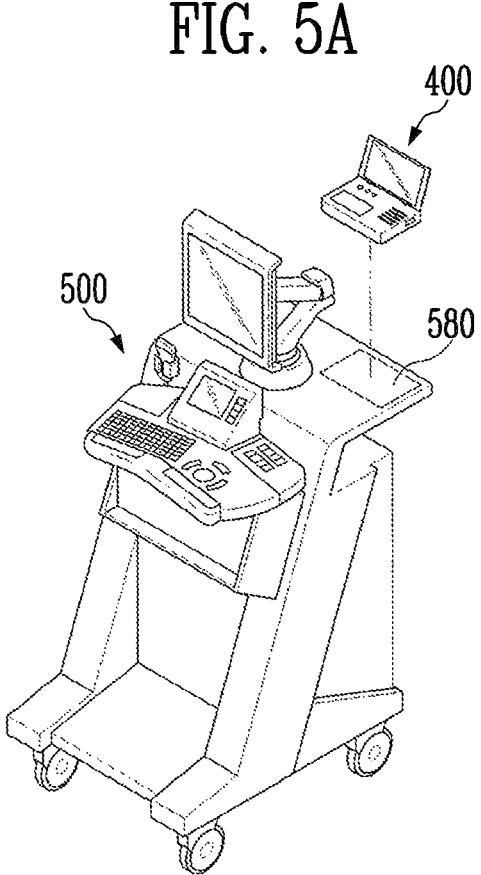
FIGS. 5A to 5C are perspective views of an ultrasound diagnosis apparatus 500 in accordance with at least one embodiment of the present disclosure.
Figure 5B:
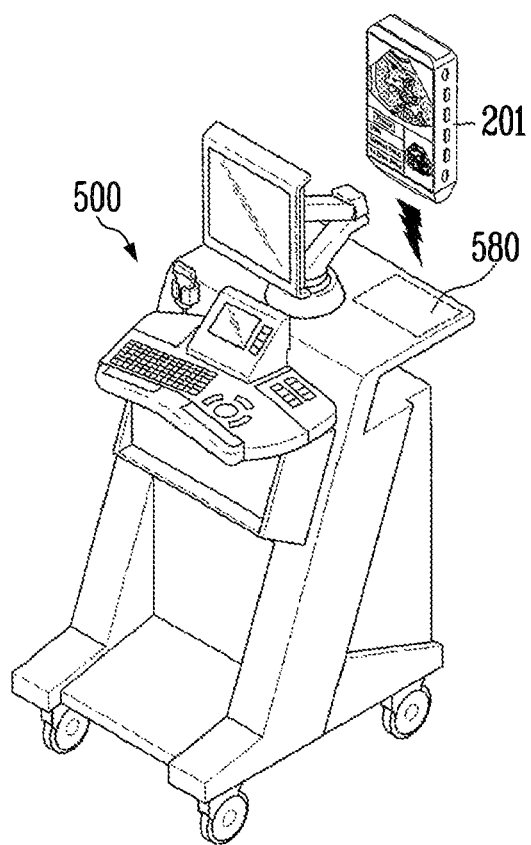
Figure 5C:
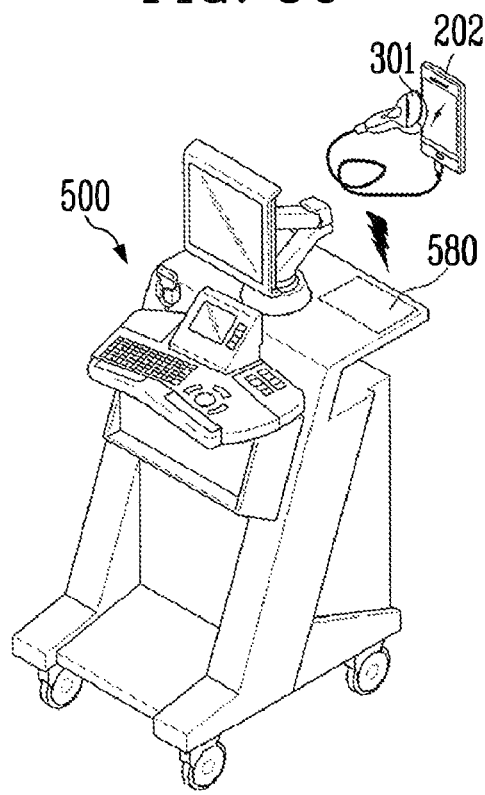

FIGS. 5A to 5C illustrate perspective views of an ultrasound diagnosis apparatus 500 in accordance with at least one embodiment of the present disclosure.

Referring to FIG. 5A, the ultrasound diagnosis apparatus used indoors or an indoor ultrasound diagnosis apparatus 500 generally refers to a non-portable ultrasound diagnosis apparatus used for ultrasound diagnosis, and such the ultrasound diagnosis apparatus 500 is also called cart base equipment. Although the ultrasound diagnosis apparatus 500 is not necessarily used only indoors, it will be referred to as an indoor ultrasound diagnosis apparatus 500 for convenience.

The indoor ultrasound diagnosis apparatus 500 may have a portable docking unit 580 connected to a portable ultrasound diagnosis apparatus 400. Since all components except for the portable docking unit 580 of the indoor ultrasound diagnosis apparatus 500 used in an embodiment of the present disclosure are generally used, a detailed description thereof will be omitted.

Unlike the portable ultrasound diagnosis apparatus 400, the indoor ultrasound diagnosis apparatus 500 has fewer restrictions in terms of size, weight, power consumption, etc., so that diagnosable area is diverse, and it may be developed with high performance. When the portable ultrasound diagnosis apparatus 400 is mounted onto the indoor ultrasound diagnosis apparatus 500, it is possible to use the portable ultrasound diagnosis apparatus 400 with high performance. However, the position at which the portable ultrasound diagnosis apparatus 400 is mounted on the indoor ultrasound diagnosis apparatus 500 may be anywhere with no limitation where it is convenient for the user to use the portable ultrasound diagnosis apparatus 400 and the indoor ultrasound diagnosis apparatus 500 at the same time, and it is not limited by FIG. 5A. Furthermore, the portable ultrasound diagnosis apparatus 400 may be connected to the indoor ultrasound diagnosis apparatus 500 through a wire or integrally.

Referring to FIGS. 5A and 5B, the portable ultrasound diagnosis apparatus 400 in FIG. 5A may correspond to a portable ultrasound diagnosis apparatus 201 in FIG. 5B.

The portable ultrasound diagnosis apparatus 400 may be integrated with a probe (not shown) including a plurality of transducer elements. Specifically, the portable ultrasound diagnosis apparatus 400 refers to an apparatus that is connected to the indoor ultrasound diagnosis apparatus 500 using a wireless or wired communication method (including Universal Serial Bus (USB)) to provide an ultrasound image to the user using received ultrasound image data. For example, the portable ultrasound diagnosis apparatus 400 may be a smart device in which an application is downloaded and installed in a smart phone.

Specifically, the portable ultrasound diagnosis apparatus 400 may be an apparatus that is connected to the indoor ultrasound diagnosis apparatus 500 through a wired or wireless communication method to provide an ultrasound image to the user using the received ultrasound image data.

For example, the wireless communication method may include at least one of short-range data communication methods including a 60 GHz (mmWave) wireless local area network (WLAN). It may be local area network (Wi-Fi), Bluetooth, ZigBee, Wi-Fi Direct (WFD), Infrared Data Association (IrDA), Bluetooth Low Energy (BLE), Near Field Communication (NFC), Wireless Broadband Internet (Wibro), globally interoperable Shared Wireless Access Protocol (SWAP) for Microwave Access (WiMAX), Wireless Gigabit Alliance (WiGig), and radio frequency (RF).

FIG. 5B illustrates an ultrasound diagnosis system in which the portable ultrasound diagnosis apparatus 201 is connected to a cart-based ultrasound diagnosis apparatus 500.

The cart-based ultrasound diagnosis apparatus 500 may be connected to the portable ultrasound diagnosis apparatus 201 using the aforementioned wireless communication method. Specifically, the portable ultrasound diagnosis apparatus 201 may include at least one wireless communication module (not shown) for performing at least one of the aforementioned wireless communication methods. Furthermore, a portable docking unit 580 in the cart-based ultrasound diagnosis apparatus 500 may include at least one wireless communication module (not shown) for performing wireless communication with the portable ultrasound diagnosis apparatus 201.

In this case, the wireless communication module in the cart-based ultrasound diagnosis apparatus 500 may be a module for performing communication according to at least one of the aforementioned wireless communication methods.

FIG. 5C illustrates an ultrasound diagnosis system in which the portable ultrasound diagnosis apparatus 202 is connected to the cart-based ultrasound diagnosis apparatus 500.

The portable ultrasound diagnosis apparatus 202 may be coupled to the probe 301 through a probe port. The portable ultrasound diagnosis apparatus 202 may be configured to generate an ultrasound image by using the ultrasound image corresponding to the ultrasound signal received by the probe 301 to display the ultrasound image on the display unit.

The cart-based ultrasound diagnosis apparatus 500 may be connected to the portable ultrasound diagnosis apparatus 202 using the aforementioned wireless communication method. The connection through wireless communication between the cart-based ultrasound diagnosis apparatus 500 and the portable ultrasound diagnosis apparatus 202 corresponds to the connection between the cart-based ultrasound diagnosis apparatus 500 and the portable ultrasound diagnosis apparatus 201, and thus a detailed description thereof will be omitted.

Hereinafter, an embodiment of an ultrasound diagnosis apparatus applicable to at least one of the ultrasound diagnosis apparatuses described with reference to FIGS. 1 to 3 will be described.

Figure 6:
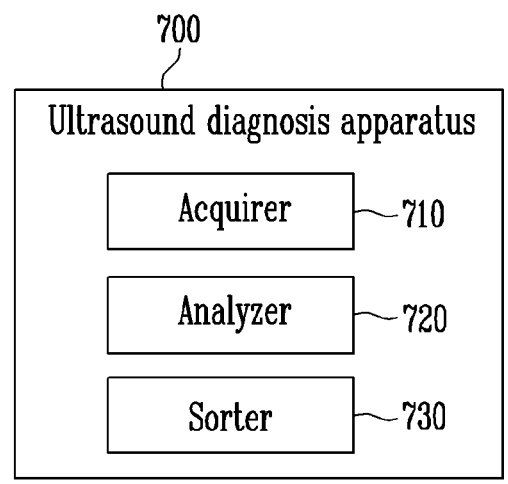
FIG. 6 is a block diagram illustrating a configuration of an ultrasound diagnosis apparatus 700 in accordance with an embodiment of the present disclosure.

FIG. 6 is a block diagram illustrating a configuration of an ultrasound diagnosis apparatus 700 in accordance with an embodiment of the present disclosure.

As shown in FIG. 6, the ultrasound diagnosis apparatus 700 according to an embodiment of the present disclosure includes an acquirer 710 configured to acquire an ultrasound image, an analyzer 720 configured to analyze appearances of a fetus using the image acquired in the acquirer 710, and a sorter 730 configured to sort the image of the fetus corresponding to a target of interest from among the fetal appearances analyzed in the analyzer 720.

An embodiment of the present disclosure may include a target-of-interest storage 740 configured to store the image sorted by the sorter 730.

The acquirer 710 of the present disclosure may be configured to acquire an ultrasound image using an ultrasound apparatus. The ultrasound image may include not only 2D, but also 3D and 4D images, so may be a 2D sagittal plane image or a 3D image as well as a 4D image that is a 3D image to which the passage of time is reflected.

The 2D sagittal plane image may include a midsagittal plane, and may also include a sagittal plane image other than the midsagittal plane. An example may include a sagittal plane in which all positions of the mouth are shown, as an image necessary to identify whether the appearance of the fetus corresponds to a target of interest.

The midsagittal plane (MSP) refers to a section corresponding to a line segment that divides the center of the fetal head among the sagittal planes.

According to an embodiment of the present disclosure, in the process of measuring the fetal head, it is possible to acquire 2D ultrasound images which are sections enabling the measurement of items such as head circumference (HC), biparietal diameter (BPD), and occipitofrontal diameter (OFD) through multiple scanning operations for the fetus.

In addition, in an embodiment of the present disclosure, it is possible to easily detect the midsagittal plane from the 3D image so as to be used as a standard section of the fetus. Specifically, the acquirer 710 of an embodiment of the present disclosure may include an image processing process for extracting a structure of the fetal falx cerebri to detect the midsagittal plane.

The falx may be detected from the 3D ultrasound image by using user input information which may be the center of the head and the face direction that the user inputs in the initial section. According to an embodiment, it is also possible to detect the midsagittal plane using the falx or automatically detect the midsagittal plane using a machine-learned method.

In an embodiment of the present disclosure, it is possible to detect the midsagittal plane through the image processing process and also detect at least one measurement section based on the detected midsagittal plane.

The analyzer 720 may be configured to analyze at least one of a mouth shape, a tongue position, and a hand and foot position of the fetus by analyzing the sagittal plane or the 3D image in which all the positions of the mouth are shown, and also analyze whether the analyzed positions of the mouth, tongue, hand, and foot of the fetus correspond to a predetermined criterion.

According to an embodiment, the analysis according to whether the predetermined criterion is met is to analyze whether the fetus is opening the mouth from whether the horizontal and vertical length of the fetal lips are more than a certain distance, and the shape of an oval corresponding to the circumference of the fetal skull is cut out. In addition, it is possible to analyze whether the distance between the mouth and the hand or foot of the fetus is close to zero (0), whether the hand or foot is put in the mouth, or whether the tongue is sticking out from a state in which a part of the upper or lower lips of the fetus is hidden by the tongue.

In relation to the analysis of whether the fetus is opening the mouth, it is determined by whether the oval shape corresponding to the circumference of the fetal skull is cut off. However, in the case of the fetus, it may be considered that the skull is not completely closed since there is a pore called the large fontanelle in the skull.

Although it may look different depending on each side image, the oval shape corresponding to the circumference of the skull may seem to be cut off even in the large fontanelle located behind the fetal skull. In this case, the position where the oval is cut off at the portion adjacent to the fetal neck may be identified as the position of the fetal mouth.

The sorter 730 may be configured to sort whether the fetal appearance corresponding to the predetermined criterion in the analyzer 720 is the appearance corresponding to the target of interest in an embodiment of the present disclosure.

In other words, it is possible to sort whether the appearance that the fetus is opening the mouth corresponds to a yawning motion, whether the appearance that the hand or foot is put in the mouth of the fetus corresponds to a hand or foot sucking motion, or whether the fetal tongue that is sticking out corresponds to a tongue sticking out motion.

The target of interest in the ultrasound diagnosis apparatus 700 of an embodiment of the present disclosure may be at least one of the yawning, hand sucking, foot sucking, and tongue sticking out motions of the fetus.

However, the target of interest is not limited to the motions listed above, and according to a predetermined criterion in the analyzer 720 and a determination criterion in the sorter 730, it is also possible to sort the appearance of opening the eyes, the appearance of touching the head, the appearance of clenching the fist.

The process of analyzing and sorting whether the object corresponds to the target of interest may be sequentially performed by the analyzer 720 and the sorter 730.

FIGS. 7A to 7D are diagrams for explaining that the ultrasound diagnosis apparatus 700 according to an embodiment of the present disclosure analyzes an appearance of a fetus to sort it as the yawning motion.

When the target of interest is the yawning motion of the fetus, the analyzer 720 may be configured to measure, through the 3D image, the vertical length from the center of an upper lip 771 to the center of a lower lip 772 of the fetus as well as the horizontal length measured by setting the left side 773 and the right side 774 of the fetal lips as both endpoints, so as to analyze that the fetus is opening the mouth when the vertical length is more than a certain multiple of the horizontal length.

Figure 7A:
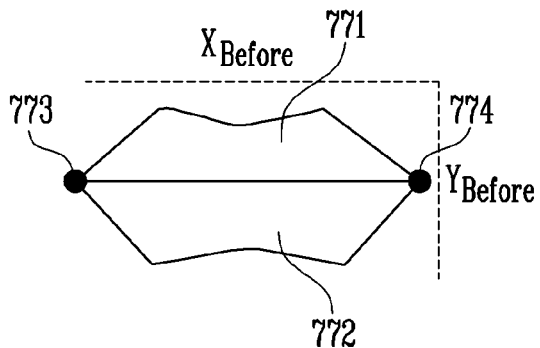
FIG. 7A is a diagram for explaining that the ultrasound diagnosis apparatus 700 in accordance with an embodiment of the present disclosure analyzes an appearance of a fetus to sort out as a yawning motion.
Figure 7B:
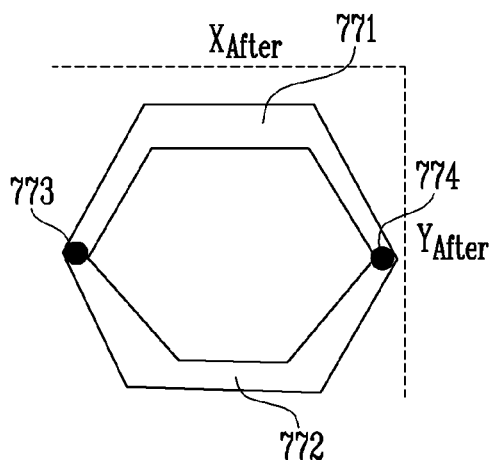
FIG. 7B is a diagram for explaining that the ultrasound diagnosis apparatus 700 in accordance with an embodiment of the present disclosure analyzes the appearance of the fetus to sort out as the yawning motion.

FIG. 7A is a diagram for explaining a process of analyzing that the fetus is opening the mouth in the analyzer 720. As shown in FIGS. 7A and 7B, when designating a horizontal length and a vertical length before opening the mouth as X (before) and Y (before), respectively, as well as the horizontal length and the vertical length after opening the mouth as X (after) and Y (after), respectively, it may be analyzed that the fetus is opening the mouth, if the vertical length over the horizontal length in the state after opening the mouth is more than a certain multiple of the vertical length over the horizontal length in the state before opening the mouth.

The certain multiple above is preferably two or more times, and it may be analyzed that the fetus is opening the mouth if a value of X(after)/Y(after) is greater than two times X(before)/Y(before) (also represented by X(before)/Y(before)×2<X(after)/Y(after)).

In addition, the analyzer 720 may be configured to analyze, through the sagittal plane in which the position of the mouth in the image is shown, that the fetus is opening the mouth when the oval is cut off at a position of the fetal mouth in the oval corresponding to the circumference of the fetal skull.

Figure 7C:
FIG. 7C is a diagram for explaining that the ultrasound diagnosis apparatus 700 in accordance with an embodiment of the present disclosure analyzes the appearance of the fetus to sort out as the yawning motion.

FIG. 7C is a 2D midsagittal plane and a diagram for analyzing whether the fetus is opening the mouth around the fetal skull. As shown in FIG. 7C, with a form 782 seeming that the oval around the fetal mouth is cut off in the oval 781 around the fetal skull, it may be identified that the fetus is opening the mouth.

As shown in FIGS. 7A to 7C, after identifying that the fetus is opening the mouth in the analyzer 720, if it is determined that the fetus is opening the mouth, the sorter 730 may determine whether the motion corresponds to the yawning motion.

The sorter 730 may be configured to classify, through the sagittal plane analyzed as opening the mouth in the analyzer 720, if it is determined that a gap between the fetal lips increases for a certain amount of time, as the yawning motion of the fetus. In other words, when the gap between the fetal lips increases in the sagittal plane in which the upper and lower portions of fetal lips are distinguished, it may be determined as the yawn. Whether the gap between the lips increases needs to be determined with the passage of time, such that it is also possible to determine whether it is the yawn by using a 4D image together.

Even if it is determined that the gap between the lips increases, there may be cases where it does not correspond to the yawning motion. For the yawning motion, the gap between lips should increase and then decrease within a certain amount of time. However, as for a case that is not the yawning motion, if the fetus keeps opening the mouth, the gap between lips may stay the same even after a certain amount of time is over after the gap increases.

In an embodiment of the present disclosure, it may be analyzed as the yawning motion when the gap between fetal lips increases for a certain amount of time while the opening of the gap between the lips does not exceed a certain amount of time.

Figure 7D:
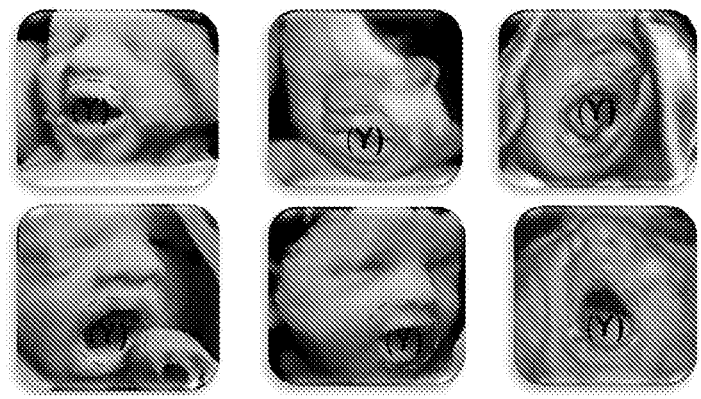
FIG. 7D is a diagram for explaining that the ultrasound diagnosis apparatus 700 in accordance with an embodiment of the present disclosure analyzes the appearance of the fetus to sort out as the yawning motion.

FIG. 7D is a diagram illustrating a case in which a 3D image is sorted in a yawning motion category by sorting the yawning motion of the fetus. In an embodiment of the present disclosure, when the appearance of the fetus corresponds to the yawning motion criterion (Y) predetermined by the analyzer 720 and the sorter 730, automatic classification may be enabled using an algorithm for sorting an image of the fetus and automatically classifying the image into the yawning motion category.

Figure 8A:
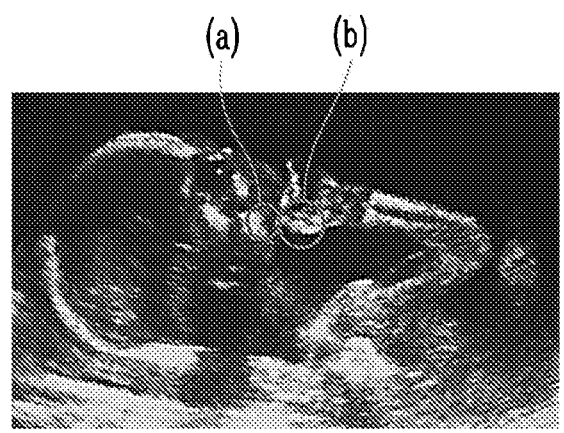
FIG. 8A is a diagram for explaining that the ultrasound diagnosis apparatus 700 in accordance with an embodiment of the present disclosure analyzes an appearance of a fetus to sort out as a hand sucking or foot sucking motion.
Figure 8B:
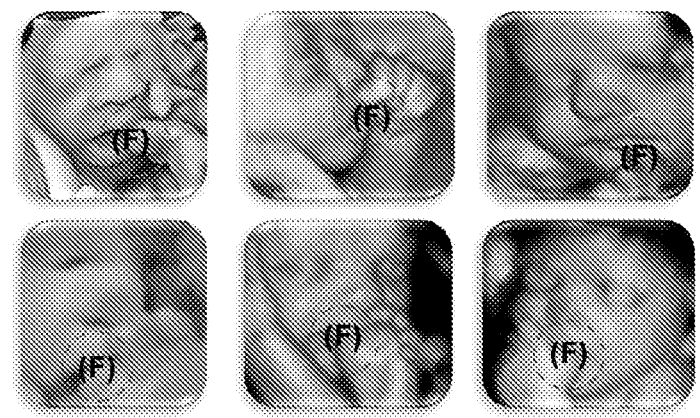
FIG. 8B is a diagram for explaining that the ultrasound diagnosis apparatus 700 in accordance with an embodiment of the present disclosure analyzes the appearance of the fetus to sort out as the hand sucking or foot sucking motion.

FIGS. 8A and 8B are diagrams for explaining that the ultrasound diagnosis apparatus 700 according to an embodiment of the present disclosure analyzes the appearance of the fetus to sort it as the hand sucking or foot sucking motion.

As in the yawning motion in FIGS. 7A to 7D, unlike the need to analyze only the position and shape of the fetal mouth, in the case of the hand or foot sucking motion or the tongue sticking out motion of the fetus, the positions of the hand or foot of the fetus or tongue of the fetus should be simultaneously analyzed together with the mouth of the fetus.

Although the fetus is performing the hand and foot sucking motion, there may be cases that the hand or foot is put at one end of the mouth. This is because the fetal tongue is sticking out only to one end of the mouth in the case of the tongue sticking out motion.

Accordingly, in the analyzer 720 for analyzing the hand or foot sucking motion and the tongue sticking out motion of an embodiment of the present disclosure, it may be predetermined whether at least one of the hands or feet is positioned around the mouth of the fetus from at least one of a 3D image and a 2D image. The two or more 2D images refer to including a sagittal plane in which the positions of the mouth are all shown as well as a measurement section.

In the ultrasound diagnosis apparatus 700 according to an embodiment of the present disclosure, when the target of interest is the hand or foot sucking motion of the fetus, the analyzer 720 may check the sagittal plane in which the positions of the mouth and hand or the mouth and foot of the fetus are all shown in the left and right directions of the fetal mouth, and measure, through the sagittal plane, the distance between the mouth and hand or the mouth and foot of the fetus, so as to analyze that the hand or foot is put in the mouth if the measured distance is less than or equal to a predetermined value.

FIG. 8A is a sagittal plane in which both the mouth and the hand of the fetus are shown, showing that the mouth (a) and the fingertip (b) of the fetus are in contact with each other and the hand of the fetus is put in the mouth as the distance between the mouth (a) and the hand (b) is measured to be less than or equal to the predetermined value.

FIG. 8B is a 3D image for the sagittal plane analyzed in the analyzer 720 as having the hand or foot put in the mouth. If it is determined that there is a movement of the fetal mouth, through the 3D image, the sorter 730 may be configured to classify as a hand sucking or foot sucking motion F of the fetus.

In the case of the hand sucking motion of the fetus, the fetus may suck in not only the thumb, but also the index finger and the little finger, and in some cases, the fetus may perform motions of sucking a plurality of fingers or the back of the hand or the fist. In an embodiment of the present disclosure, in consideration of the case that the fetus may suck in various positions of the hand, by presetting criteria in the analyzer 720 and the sorter 730 for the position of the palm and each finger and the relationship between the hand and the mouth so as to analyze the motion in the analyzer 720 and the sorter 730, it is possible to sort out various hand sucking motions.

Also in the case of the foot sucking motion, since the fetus is not only sucking the big toe, it is possible to sort the motion by presetting criteria for cases of sucking the index toe or the little toe or sucking two or more toes.

In an embodiment of the present disclosure, in some cases, within the category of hand sucking or foot sucking, it is possible to provide the mother by sorting out even the sucking part.

Figure 9A:
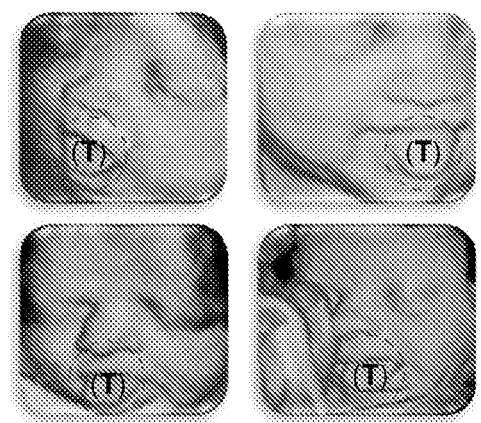
FIG. 9A is a diagram for explaining that the ultrasound diagnosis apparatus 700 in accordance with an embodiment of the present disclosure analyzes an appearance of a fetus to sort out as a tongue sticking out motion.
Figure 9B:
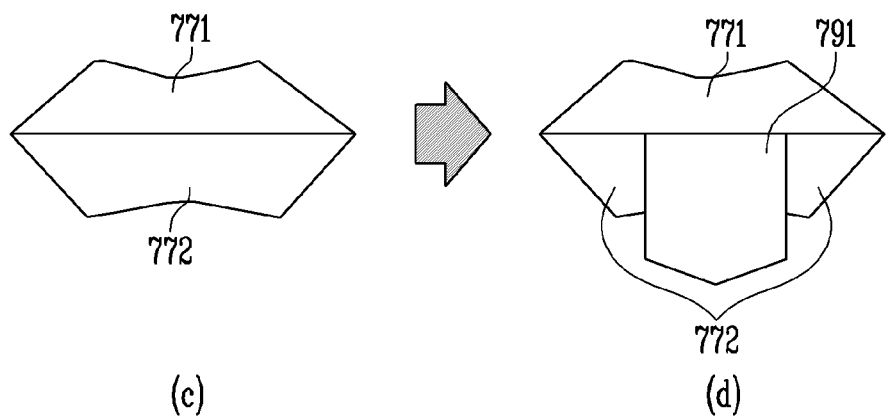
FIG. 9B is a diagram for explaining that the ultrasound diagnosis apparatus 700 in accordance with an embodiment of the present disclosure analyzes the appearance of the fetus to sort out as the tongue sticking out motion.
Figure 9C:
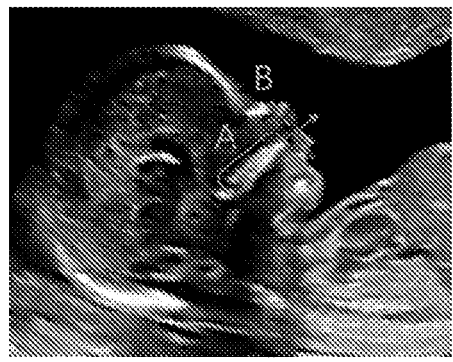
FIG. 9C is a diagram for explaining that the ultrasound diagnosis apparatus 700 in accordance with an embodiment of the present disclosure analyzes the appearance of the fetus to sort out as the tongue sticking out motion.

FIG. 9A to 9C are diagrams for explaining that the ultrasound diagnosis apparatus 700 according to an embodiment of the present disclosure analyzes an appearance of a fetus to sort it as a tongue sticking out motion T.

FIG. 9A shows the appearance that the upper lip 771 or lower lip 772 is hidden by a tongue 791 due to the tongue coming out of the fetal mouth from among 3D images in which both the mouth and tongue of the fetus are shown. FIG. 9B is a diagram illustrating a case in which a part of the upper lip 771 or lower lip 772 is invisible by being hidden by the tongue 791 while the appearance changes from (c) to (d) as a result of tracking with the passage of time.

When the target of interest is the tongue sticking out motion T, the analyzer 720 checks a 3D image in which both the mouth and tongue 791 of the fetus are shown in the left and right directions of the fetal mouth (FIG. 9A), and when it is determined that a part of the upper lip 771 or lower lip 772 of the fetus is invisible by being hidden by the tongue 791 (FIG. 9B), it may be analyzed that the fetus is sticking out the tongue 791.

As shown in FIG. 9C, the sorter 730 may sort, through the sagittal plane in which the positions of the mouth in the image analyzed in the analyzer 720 as having the tongue stick out are all shown, whether the motion is the tongue sticking out motion T. FIG. 9C is a midsagittal plane marked with the fetal tongue position A and the mouth base line B. If it is determined that the fetal tongue position A is beyond the mouth base line B, it may be classified as the tongue sticking out motion T of the fetus.

The ultrasound diagnosis apparatus 700 of an embodiment of the present disclosure may include a display unit 760 configured to display the sorted image on a screen.

The image displayed on the display unit 760 may be a 3D image including an image of a fetus corresponding to the target of interest, or a 4D image including the passage of time over the 3D image. Furthermore, since a 2D image that is a sagittal plane acquired by the acquirer 710 may be displayed, the image displayed on the display unit 760 is not limited to the 3D image, and may be at least one of 2D images, 3D images, and 4D images including the passage of time.

According to an embodiment of the present disclosure, when the image sorted by the sorter 730 overlaps with an image having the same fetal appearance, an extractor 750 configured to extract a high-quality image from among the overlapping images may be further included. In this case, the display unit 760 may be configured to display the extracted high-quality image.

The display unit 760 may be configured to simultaneously display a plurality of sorted images, and further include a selector 770 capable of selecting an image to be displayed on the screen from among the sorted images to display an image depending on the selection of a doctor or a mother.

In addition, the display unit 760 may be configured to display a notification when the appearance of the fetus corresponds to the target of interest, and the notification may be a lighting type using light or a sound type using a buzzer, but the type of notification is not limited to the types listed above.

For example, when the fetus yawns, a different notification sound may be set according to the fetal motion, such as the notification sound that may correspond to the yawning sound.

By notifying the doctor of the moment when the appearance of the fetus corresponds to the target of interest through the notification display on the display unit 760, the doctor may check the ultrasound image at the moment of notification and further store the image determined by the doctor.

FIG. 10 illustrates a flowchart of an ultrasound diagnosis method in accordance with an embodiment of the present disclosure.

As shown in FIG. 10, the ultrasound diagnosis method according to an embodiment of the present disclosure may include acquiring, by the acquirer 710, an ultrasound image S100, analyzing, by the analyzer 720, the appearance of a fetus using the acquired image S200, and sorting, by the sorter 730, an image of the fetus corresponding to the target of interest among the analyzed fetal appearance S300.

Acquiring of the ultrasound image S100 may include detecting, by the acquirer 710, a 3D ultrasound image as a sagittal plane S110.

The analyzing of the appearance of the fetus using the acquired image S200 may be analyzing, by the analyzer 720, the current appearance of the fetus by determining whether the fetus is opening the mouth, a hand or foot is put in the mouth, or the tongue is sticking out.

The method may include sorting out, by the sorter 730, an image of the fetus corresponding to a target of interest from among the fetal images analyzed in the analyzer 720 S300. The sorting of the image S300 may include determining whether the fetal appearance analyzed in the analyzer 720 corresponds to the target of interest S301, and classifying the fetal image determined as the target of interest S302.

The determining of the yawning motion of the fetus according to an embodiment may include measuring, by the analyzer 720, through the 3D image, the vertical length from the center of the upper lip to the center of the lower lip of the fetus as well as the horizontal length measured by setting the left and right sides of the fetal lips as both endpoints, so as to analyze that the fetus is opening the mouth when the vertical length is more than a certain multiple of the horizontal length S210.

Thereafter, the method may include classifying, by the sorter 730, the motion as the yawning motion of the fetus, if it is determined that the gap between the lips increases for a certain amount of time, through the sagittal plane of the image analyzed in the analyzer 720 as opening the mouth S310.

In addition, the method may include analyzing, by the analyzer 720, that the fetus is opening the mouth, when the oval is cut off at the corresponding position of the fetal mouth in the oval corresponding to the circumference of the fetal skull, through the sagittal plane including the mouth in the image S220.

The determining of the hand sucking motion of the fetus according to an embodiment may include checking, by the analyzer 720, the sagittal plane in which both the positions of the hands and mouth of the fetus are shown in the left and right directions of the fetal mouth S230, and measuring, by the analyzer 720, through sagittal plane in which the position of the mouth is shown, the distance between the mouth and hand of the fetus and analyzing that the hand is put in the mouth if the analyzed distance is less than or equal to a predetermined value S240.

Thereafter, the method may include classifying, by the sorter 730, as the hand sucking motion, if it is determined that there is a movement of the mouth of the fetus through the 3D image of the image analyzed by the analyzer 720 that the hand is put in the mouth S320.

The determining of the foot sucking motion of the fetus according to an embodiment may include checking, by the analyzer 720, the sagittal plane in which both the positions of the foot and mouth of the fetus are shown in the left and right directions of the fetal mouth S230, and measuring, by the analyzer 720, through the sagittal plane, the distance between the mouth and the foot of the fetus and analyzing that the foot is put in the mouth if the analyzed distance is less than or equal to the predetermined value S250.

Thereafter, the method may include classifying, by the sorter 730, as the foot sucking motion of the fetus, if it is determined that there is a movement of the mouth of the fetus, through the 3D image of the image analyzed by the analyzer 720 that the foot is put in the mouth S330.

The determining of the tongue sticking out motion of the fetus according to an embodiment may include checking, by the analyzer 720, the 3D image in which both the mouth and the tongue of the fetus are shown in the left and right directions of the fetal mouth S260, and analyzing, by the analyzer 720, through the 3D image, that the fetus is sticking out the tongue if a part of the upper lip 771 or lower lip 772 of the fetus is invisible by being hidden by the tongue S270.

Thereafter, the method may include classifying, by the sorter 730, as the tongue sticking out motion of the fetus, through the sagittal plane including the mouth of the image analyzed by the analyzer 720 as the tongue sticking out motion, if it is determined that the position of the fetal tongue is beyond the fetal mouth base line S340.

The method may include storing, by the target-of-interest storage 740, the image sorted in the sorter 730 S400, wherein all images may be stored when the sorted images overlap, but depending on embodiments, the high-quality image sorted by the extractor 750 may be extracted and stored.

FIG. 11 is a diagram for explaining content displayed on the display unit of the ultrasound diagnosis apparatus 700 in accordance with an embodiment of the present disclosure.

A method of storing an ultrasound image of an embodiment of the present disclosure may include displaying, by the display unit 760, the sorted image on a screen S500.

According to an embodiment, the display unit 760 may further include a selector 770 configured to select an image to be displayed on the screen from among the sorted images. For example, only the yawning motion may be selected to be displayed from among the targets of interest.

Only the yawning, hand sucking, foot sucking, and tongue sticking out motions have been described herein as motions including the face among the appearance of the fetus. Therebeside, images for the motions of opening the eyes and touching the head shown around the face may be sorted and displayed as a user predetermines a criterion and designate as the target of interest. It may be possible to sort the motion of spreading or clenching the fingers or toes around the hands and feet of the fetus, not only the face.

According to an embodiment, as shown in FIG. 11, by selecting the yawn and hand sucking motions in the face category and selecting the toe in the hand and foot category, it is possible to sort out an image of the toe based on set criteria for the yawning and hand sucking motions and toes of the fetus.

In addition, depending on the selection, an image including the spine and chest of the fetus may be sorted. In this case, in determining whether the fetus is malformed, it is also possible to sort out the image that is easy to identify the number and location of bones corresponding to the diagnostic category.

FIG. 12 is a diagram for explaining content displayed on the display unit of the ultrasound diagnosis apparatus 700 in accordance with another embodiment of the present disclosure.

According to an embodiment, the display unit 760 may be configured to display a pregnancy period of a mother corresponding to the fetal image. As shown in FIG. 12, images stored in the regularly performed ultrasound examination may be classified by period of pregnancy and fetal appearance to be displayed together.

The present disclosure is to easily provide an image that a mother desires without a separate sorting operation in the ultrasound examination process. Each time the mother visits a hospital to have the ultrasound examination, the mother is able to observe the growth process of the fetus in a glance by classifying the provided images by the period and appearance to provide the images to the mother.

The image stored in the ultrasound diagnosis apparatus 700 according to an embodiment of the present disclosure may be connected to an external device (e.g., a server, a medical device, a portable device (smartphones, tablet PCs, wearable devices, etc.)) through communication. In some embodiments, the content displayed on the display unit 760 may be checked through a personal portable device of the mother.

However, the disclosed embodiments may be implemented in the form of a recording medium storing instructions executable by a computer. Instructions may be stored in the form of program code. When executed by a processor, program modules may be generated to perform operations of the disclosed embodiments. The recording medium may be implemented as a computer-readable recording medium.

The computer-readable recording medium includes any type of recording media in which instructions readable by the computer are stored. Examples may include a read only memory (ROM), a random access memory (RAM), a magnetic tape, a magnetic disk, a flash memory, and an optical data storage.

The disclosed embodiments have been described with reference to the accompanying drawings as described above. Those skilled in the art to which the present disclosure pertains will understand that the present disclosure may be practiced in forms different from the disclosed embodiments without changing the technical spirit or essential features of the present disclosure. The disclosed embodiments are illustrative and should not be construed as limiting.

What is claimed is:

1. An ultrasound diagnosis apparatus, comprising:
memory storing one or more instructions; and
at least one processor configured to execute the one or more instructions,
wherein the one or more instructions, when executed by the at least one processor, cause the ultrasound diagnosis apparatus to:
acquire an ultrasound image;
analyze whether one or more body parts included in an appearance of a fetus are corresponding to a predetermined criterion based on the acquired ultrasound image, and
sort out the appearance of the fetus corresponding to a motion of interest related to the one or more body parts.

2. The ultrasound diagnosis apparatus of claim 1, wherein the one or more instructions, when executed by the at least one processor, cause the ultrasound diagnosis apparatus to: measure, through a 3D image, a vertical length from a center of an upper lip to the center of a lower lip of the fetus as well as a horizontal length measured by setting left and right sides of the fetal lips as both endpoints so as to analyze that the fetus is opening its mouth when the vertical length is more than a predetermined multiple of the horizontal length, and
through a sagittal plane representing a position of the mouth in the 3D image and an additional ultrasound image, when it is determined that a gap between the lips of the fetus increases for a predetermined amount of time classify the appearance of the fetus as the yawning motion of the fetus.

3. The ultrasound diagnosis apparatus of claim 2, wherein the one or more instructions, when executed by the at least one processor, cause the ultrasound diagnosis apparatus to analyze, through the sagittal plane representing the position of the mouth and a circumference of a head of the fetus, that the fetus is opening its mouth when a boundary line corresponding to the circumference of the head of the fetus is cut off at the position of the fetal mouth.

4. The ultrasound diagnosis apparatus of claim 1, wherein the motion of interest is dependent on a relationship between the one or more body parts.

5. The ultrasound diagnosis apparatus of claim 1, wherein the one or more instructions, when executed by the at least one processor, cause the ultrasound diagnosis apparatus to determine whether at least one of a hand and a foot of the fetus is positioned around a mouth of the fetus from at least one of a 3D image and a 2D image.

6. The ultrasound diagnosis apparatus of claim 5, wherein the one or more instructions, when executed by the at least one processor, cause the ultrasound diagnosis apparatus to, after identifying a sagittal plane in the at least one of the 3D image or the 2D image in which at least one of the hand or foot of the fetus is positioned around the mouth of the fetus, measure, through the sagittal plane, a distance between the mouth and hand or the mouth and foot of the fetus so as to analyze that the hand or foot of the fetus is put in the mouth when the measured distance is less than or equal to a predetermined value.

7. The ultrasound diagnosis apparatus of claim 6, wherein the one or more instructions, when executed by the at least one processor, cause the ultrasound diagnosis apparatus to, based on the 3D image in which the at least one of the hand or foot of the fetus is positioned in the mouth of the fetus and an additional ultrasound image, when it is determined that there is a movement of the fetal mouth, classify the appearance of the fetus as a hand sucking or foot sucking motion of the fetus.

8. The ultrasound diagnosis apparatus of claim 5, wherein the one or more instructions, when executed by the at least one processor, cause the ultrasound diagnosis apparatus to, after identifying the 3D image representing the mouth and a tongue of the fetus, analyze, through the 3D image, that the fetus is sticking out the tongue when a part of an upper or lower lip of the fetus is invisible by being hidden by the tongue.

9. The ultrasound diagnosis apparatus of claim 5, wherein the one or more instructions, when executed by the at least one processor, cause the ultrasound diagnosis apparatus to, through a sagittal plane, when it is determined that a position of a tongue of the fetus is beyond a base line of the fetal mouth, classify the appearance of the fetus as a tongue sticking out motion of the fetus.

10. An ultrasound diagnosis method performed by an ultrasound diagnosis apparatus, comprising:
    acquiring an ultrasound image;
    analyzing whether one or more body parts included in an appearance of a fetus are corresponding to a predetermined criterion based on the acquired ultrasound image; and
    sorting out the appearance of the fetus corresponding to a motion of interest related to the one or more body parts.

11. The ultrasound diagnosis method of claim 10, wherein the motion of interest is dependent on a relationship between the one or more body parts.

12. The ultrasound diagnosis method of claim 10, further comprising:
    determining a yawning motion of the fetus,
    wherein the determining of the yawning motion of the fetus comprises:
    measuring through a 3D image, a vertical length from a center of an upper lip to the center of a lower lip of the fetus as well as a horizontal length measured by setting left and right sides of the fetal lips as both endpoints so as to analyze that the fetus is opening its mouth when the vertical length is more than a predetermined multiple of the horizontal length; and
    through a sagittal plane representing a position of the mouth in the 3D image and an additional ultrasound image, when it is determined that a gap between the lips of the fetus increases for a predetermined amount of time, classifying the appearance of the fetus as the yawning motion of the fetus.

13. The ultrasound diagnosis method of claim 12, comprising:
    analyzing through the sagittal plane representing the position of the mouth and a circumference of a head of the fetus in the ultrasound image, that the fetus is opening the mouth, when a boundary line corresponding to the circumference of the head of the fetal is cut off at the position corresponding to the fetal mouth.

14. The ultrasound diagnosis method of claim 10, further including:
    determining a hand sucking or foot sucking motion of the fetus,
    wherein the determining of the hand sucking or foot sucking motion of the fetus comprises:
    checking a sagittal plane in which at least one of the hand or foot of the fetus is positioned around the mouth of the fetus;
    measuring through the sagittal plane, a distance between the mouth and hand or the mouth and foot of the fetus to analyze that the hand or foot is positioned in the mouth
    when the analyzed distance is less than or equal to a predetermined value; and
    based on a 3D image in which the at least one of the hand or foot is positioned in the mouth of the fetus and an additional ultrasound image, when it is determined that there is a movement of the fetal mouth, classifying the appearance of the fetus, as the hand sucking or foot sucking motion of the fetus.

15. The ultrasound diagnosis method of claim 10, further comprising:
    determining a tongue sticking out motion of the fetus,
    wherein the determining of the tongue sticking out motion of the fetus comprises:
    identifying a 3D image in which both a mouth and a tongue of the fetus;
    analyzing through the 3D image, that the fetus is sticking out the tongue when a part of an upper or a lower lip of the fetus is invisible by being hidden by the tongue; and
    through a sagittal plane including the mouth in the ultrasound image as the fetus sticking out the tongue, classifying the appearance of the fetus as the tongue sticking out motion of the fetus when it is determined that a position of the fetal tongue is beyond a base line of the fetal mouth.

* * * * *